United States Patent
Bissery (12)

(10) Patent No.: US 6,239,167 B1
(45) Date of Patent: May 29, 2001

(54) ANTITUMOR COMPOSITIONS CONTAINING TAXANE DERIVATIVES

(75) Inventor: Marie-Christine Bissery, Vitry sur Seine (FR)

(73) Assignee: Aventis Pharma S.A., Antony (FR)

(*) Notice: Subject to any disclaimer, the term of this patent is extended or adjusted under 35 U.S.C. 154(b) by 0 days.

(21) Appl. No.: 09/506,902

(22) Filed: Feb. 18, 2000

Related U.S. Application Data

(62) Division of application No. 09/371,520, filed on Aug. 10, 1999, which is a continuation of application No. 09/182,900, filed on Oct. 30, 1998, now abandoned, which is a division of application No. 08/967,036, filed on Nov. 10, 1997, now Pat. No. 5,908,835, which is a division of application No. 08/424,470, filed as application No. PCT/FR93/01096 on Nov. 8, 1993, now Pat. No. 5,728,687.

(30) Foreign Application Priority Data

Nov. 10, 1992 (FR) .................................................. 92 13525

(51) Int. Cl.⁷ .................................................. A61K 31/35
(52) U.S. Cl. .................................. 514/449; 514/2; 514/6; 514/8; 514/184; 514/492; 514/836; 514/922
(58) Field of Search ............................. 514/2, 6, 8, 184, 514/449, 492, 836, 922

(56) References Cited

U.S. PATENT DOCUMENTS

| | | |
|---|---|---|
| 4,857,653 | 8/1989 | Colin et al. . |
| 4,892,735 | 1/1990 | Harrap . |
| 5,494,683 | 2/1996 | Liversidge et al. . |
| 5,645,988 | 7/1997 | Vande Woude et al. . |

OTHER PUBLICATIONS

Mirabelli et al., "A Murine Model to Evaluate the Ability of in Vitro Clonogenic Assays to Predict the Response to Tumors In Vivo," *Cancer Res.* 48:5447–5454 (1988).
Rowinsky et al., Sequences of Taxol and Cisplatin: A Phase I and Pharmacologic Study, J. of Clin. Oncology, vol. 9(9):1692–1703 (1991).
Rowinsky et al., The Clinical Pharmacology and Use of Antimicrotubule Agents in Cancer Chemotherapeutics, Pharmac. Ther., vol. 52:35–84 (1991).
Bissery et al., Abstract 2645, Proceedings of the AACR 33:443 (Mar. 1992).
Bissery et al., "Preclinical Profile of Docetaxel (Taxotere): Efficacy as a Single Agent and in Combination," Seminars in Oncology, vol. 22, No. 6, Suppl 13:3–16 (1995).
Bissery et al., "The Taxoids," Cancer Therapeutics: Experimental and Clinical Agents, pp. 175–193 (1995).
Bissery et al., Abstract 1599, "Preclinical In Vivo Activity of Docetaxel Containing Combinations," Proceedings of the ASCO vol. 14:489 (1995).
Bissery et al., Abstract 50, "Preclinical In Vivo Evaluation of Docetaxel (Taxotere®) Containing Combinations," Proc. of the Cytoskeleton and Cancer, p. 50 (Sep. 17–20, 1995).

*Primary Examiner*—Frederick Krass
(74) *Attorney, Agent, or Firm*—Finnegan, Henderson, Farabow, Garrett & Dunner L.L.P.

(57) ABSTRACT

Disclosed are compositions comprising 1) taxol, taxotere, or derivatives thereof and 2) a platinum coordination complex such as cisplatin, the compositions exhibiting therapeutic synergy.

9 Claims, No Drawings

ANTITUMOR COMPOSITIONS CONTAINING TAXANE DERIVATIVES

This is a division of application Ser. No. 09/371,520, filed Aug. 10, 1999, which is a continuation of Ser. No. 09/182,900, filed Oct. 30, 1998, now abandoned which is a divisional of application Ser. No. 08/967,036, filed Nov. 10, 1997, now U.S. Pat. No. 5,908,835 which is a divisional of 08/424,470, filed May 9, 1995, now U.S. Pat. No. 5,728,687, which is based on International Application No. PCTFR9301096, filed Nov. 8, 1993, which is based on French Application No. 92 13525, filed Nov. 10, 1992, all of which are incorporated herein by reference.

The present invention relates to combinations of taxol, Taxotere and their analogues and substances which are therapeutically useful in the treatment of neoplastic diseases.

Taxol, Taxotere and their analogues, which possess noteworthy antitumour and antileukaemic properties, are especially useful in the treatment of cancers of the ovary, breast or lung.

The preparation of taxol, Taxotere and their derivatives form the subject, for example, of European Patents EP 0,253,738 and EP 0,253,739 and International Application PCT WO 92/09,589.

Generally, the doses used, which depend on factors distinctive to the subject to be treated, are between 1 and 10 mg/kg administered intraperitoneally or between 1 and 3 mg/kg administered intravenously.

It has now been found, and this forms the subject of the present invention, that the efficacy of taxol, Taxotere and their analogues may be considerably improved when they are administered in combination with at least one substance which is therapeutically useful in anticancer treatments and has a mechanism identical to or different from this of taxane derivatives.

Among substances which may be used in association or in combination with taxol, Taxotere or their analogues, there may be mentioned alkylating agents such as cyclophosphamide; isosfamide, melphalan, hexamethylmelamine, thiotepa or dacarbazine, antimetabolites such as pyrimidine analogues, for instance 5-fluorouracil and cytarabine or its analogues such as 2-fluorodeoxycytidine, or folic acid analogues such as methotrexate, idatrexate or trimetrexate, spindle poisons including vinca alkaloids such as vinblastine or vincristine or their synthetic analogues such as navelbine, or estramustine or taxoids, epidophylloptoxins such as etoposide or teniposide, antibiotics such as daunorubicine, doxorubicin, bleomycin or mitomycin, enzymes such as L-asparaginase, topoisomerase inhibitors such as camptothecin derivatives chosen from CPT-11 and topotecan or pyridobenzoindole derivatives, and various agents such as procarbazine, mitoxantrone, platinum coordination complexes such as cisplatin or carboplatin, and biological response modifiers or growth factor inhibitors such as interferons or interleukins.

Moreover, since the activity of the. products depends on the doses used, it is possible to use higher doses and to increase the activity while decreasing the toxicity phenomena or delaying their onset by combining growth factors of the haematopoietic type such as G-CSF or GM-CSF or certain interleukins with taxol, Taxotere, their analogues or their combinations with other therapeutically active substances.

The combinations or associations according to the invention enable the phenomena of pleiotropic resistance or "multi-drug resistance" to be avoided to delayed.

More especially, the invention relates to combinations of taxol, Taxotere and their analogues with vinca alkaloids, cyclophosphamide, 5-fluorouracil, doxorubicin, cisplatin and etoposide.

The improved efficacy of a combination according to the invention may be demonstrated by determination of the therapeutic synergy.

The efficacy of a combination according to the invention may also be characterized by adding the actions of each constituent.

A combination manifests therapeutic synergy if it is therapeutically superior to one or other of the constituents used at its optimum dose [T. H. CORBETT et al., Cancer Treatment Reports, 66, 1187 (1982)].

To demonstrate the efficacy of a combination, it may be necessary to compare the maximum tolerated dose of the combination with the maximum tolerated dose of each of the separate constituents in the study in question. This efficacy may be quantified, for example by the $\log_{10}$ cells killed, which is determined according to the following formula:

$$\log_{10}\text{cells killed} = T - C \text{ (days)}/3.32 \times T_d$$

in which T–C represents the time taken for the cells to grow, which is the mean time in days for the tmours of the treated group (T) and the tumours of the treated group (C) to have reached a predetermined value (1 g for example), and $T_d$ represents the time in days needed for the volume of the tumour to double in the control animals [T. H. CORBETT et al., Cancer, 40, 2660.2680 (1977); F. M. SCHABEL et al., Cancer Drug Development, Part B, Methods in Cancer Research, 17, 3–51, New York, Academic Press Inc. (1979)]. A product is considered to be active if $\log_{10}$ cells killed is greater than or equal to 0.7. A product is considered to be very active if $\log_{10}$ cells killed is greater than 2.8.

The combination, used at its own maximum tolerated dose, in which each of the constituents will be present at a dose generally not exceeding its maximum tolerated dose, will manifest therapeutic synergy when the $\log_{10}$ cells killed is greater than the value of the $\log_{10}$ cells killed of the best constituent when it is administered alone.

The efficacy of the combinations on solid tumours may be determined experimentally in the following manner:

The animals subjected to the experiment, generally mice, are subcutaneously grafted bilaterally with 30 to 60 mg of a tumour fragment on day 0. The animals bearing tumours are mixed before being subjected to the various treatments and controls. In the case of treatment of advanced tumours, tumours are allowed to develop to the desired size, animals having insufficiently developed tumours being eliminated. The selected animals are distributed at random to undergo the treatments and controls. Animals not bearing tumours may also be subjected to the same treatments as the tumour-bearing animals in order to be able to dissociate the toxic effect from the specific effect on the tumour. Chemotherapy generally begins from 3 to 22 days after grafting, depending on the type of tumour, and the animals are observed every day. The different animal groups are weighed 3 or 4 times a week until the maximum weight loss is attained, and the groups are then weighed at least once a week until the end of the trial.

The tumours are measured 2 or 3 times a week until the tumour reaches approximately 2 g, or until the animal dies if this occurs before the tumour reaches 2 g. The animals are autopsied when sacrificed.

The antitumour activity is determined in accordance with the different parameters recorded.

For a study of the combinations on leukaemias, the animals are grafted with a particular number of cells, and the antitumour activity is determined by the increase in the survival time of the treated mice relative to the controls. The product is considered to be active if the increase in survival time is greater than 27%, and is considered to be very active if it is greater than 75% in the case of P388 leukaemia.

The results obtained with combinations of Taxotere and various chemotherapeutic agents, such as cyclophosphamide (alkylating agent), 5-fluorouracil (antimetabolite), etoposide (semisynthetic podophyllotoxin agent) and vincristine (vinca alkaloid), the combinations being used at their optimum dose, are given as examples in the following tables.

TABLE 1

Activity of the combination Taxotere + cyclophosphamide at the optimum dose against advanced MA13/c mammary adenocarcinoma grafted subcutaneously

| Product | Dose mg/kg/injection i.v. | Administration on days: | Total dose mg/kg | $\log_{10}$ cells killed |
|---|---|---|---|---|
| Taxotere | 15 | 14, 17, 20 | 45 | 2.8 |
| cylcophosphamide | 118 | 14 | 118 | 1.3 |
| Taxotere + cyclophosphamide | 7.5 90.0 | 14, 17, 20, 14 | 22.5 90 | 3.4 |

TABLE 2

Activity of the combination Taxotere + etoposide at the optimum dose against early B16 melanoma grafted subcutaneously

| Product | Dose mg/kg/injection i.v. | Administration on days: | Total dose mg/kg | $\log_{10}$ cells killed |
|---|---|---|---|---|
| Taxotere | 17.5 | 4, 7, 10, 13 | 70 | 2.8 |
| Etoposide | 46.2 | 4, 7, 10, 13 | 184.8 | 2.8 |
| Taxotere + etoposide | 15.7 13.8 | 4, 7, 10, 13 (simultaneous) | 62.8 55.2 | 4.1 |

TABLE 3

Activity of the combination Taxotere + 5-fluorouracil at the optimum dose against advanced C38 colon adenocarcinoma grafted subcutaneously

| Product | Dose mg/kg/injection i.v. | Administration on days: | Total dose mg/kg | $\log_{10}$ cells killed |
|---|---|---|---|---|
| Taxotere | 22 | 21, 25, 29, 33 | 88.0 | 1.4 |
| 5-fluorouracil | 43.4 | 21, 25, 29, 33 | 173.6 | 1.1 |
| Taxotere + 5-fluorouracil | 17.6 27.0 | 21, 25, 29, 33 (simultaneous) | 70.4 108.0 | 4.8 |

TABLE 4

Activity of the combination Taxotere + vincristine at the optimum dose against P388 leukaemia ($10^6$ cells i.p.)

| Product | Dose mg/kg/injection i.v. | Administration on days: | Total dose mg/kg | $\log_{10}$ cells killed |
|---|---|---|---|---|
| Taxotere | 17.5 | 4, 7, 10, 13 | 70 | 2.8 |
| vincristine | 46.2 | 4, 7, 10, 13 | 184.8 | 2.8 |
| Taxotere + vincristine | 21.75 1.2 | 1, 4, 7 (simultaneous) | 65.25 3.6 | 62 |
| Taxotere + vincristine | 21.75 1.2 | 1, 4, 7 (4 hours apart) | 65.25 3.6 | 77 |

The present invention also relates to pharmaceutical compositions containing the combinations according to the invention.

The products of which the combination are composed may be administered simultaneously, separately or spaced out over a period of time so as to obtain the maximum efficacy of the combination; it being possible for each administration to vary in its duration from a rapid administration to a continuous perfusion.

As a result, for the purposes of the present invention, the combinations are not exclusively limited to those which are obtained by physical association of the constituents, but also to those which permit a separate administration, which can be simultaneous or spaced out over a period of time.

The compositions according to the invention are preferably compositions which can be administered parentally. However, these compositions may be administered orally or intraperitoneally in the case of localized regional therapies.

The compositions for parental administration are generally pharmaceutically acceptable, sterile solutions or suspensions which may optionally be prepared as required at the time of use. For the preparation of non-aqueous solutions or suspensions, natural vegetable oils such as-olive oil, sesame oil or liquid petroleum or injectable organic esters such as ethyl oleate may be used. The sterile aqueous solutions can consist of a solution of the product in water. The acueous solutions are suitable for intravenous administration provided the pH is appropriately adjusted and the solution is made isotonic, for example with a sufficient amount of sodium chloride or glucose. The sterilization may be carried out by heating or by any other means which does not adversely affect the composition. The combinations may also take the form of liposomes or the form of an association with carriers as cyclodextrins or polyethylene glycols.

The compositions for oral or intraperitoneal administration are Dreferably aqueous suspensions or solutions.

In the combinations according to the invention, the application of the constituents of which may be simultaneous, separate or spaced out over a period of time, it is especially advantageous for the amount of taxane derivative to represent from 10 to 90% by weight of the combination, it being possible for this content to vary in accordance with the nature of the associated substance, the efficacy sought and the nature of the cancer to be treated.

The combinations according to the invention are especially useful in the treatment of cancers of the breast, ovary or lung. In particular, they can afford the advantage of being able to employ the constituents at considerably lower doses than those at which they are used alone.

The example which follows illustrates a combination according to the invention.

EXAMPLE 10-cm$^3$ ampoules containing 100 mg of Taxotere are prepared, for intravenous administration, according to the usual technique.

5-cm$^3$ ampoules containing 100 mg of etoposide are prepared, for intravenous administration, according to the usual technique.

These solutions are administered simultaneously, after appropriate dilution, by perfusion.

The treatment may be repeated several times daily or weakly until there is a partial or total remission or a cure.

What is claimed is:

1. A combination having therapeutic synergy comprising at least one taxane selected from the group consisting of taxol, Taxotere and derivatives thereof in combination with an effective amount of a platinum coordination complex.

2. The combination according to claim 1, wherein said platinum coordination complex is cisplatin.

3. The combination according to claim 1, further comprising one or more growth factors selected from the group consisting of G-CSF, GM-CSF and interleukin.

4. The combination according to claim 1, wherein said at least one taxane is present in an amount ranging from 10% to 90% by weight.

5. The combination according to claim 2 for the treatment of metastatic breast cancer.

6. The combination according to claim 1, wherein said at least one taxane and said effective amount of a platinum coordination complex are administered separately or simultaneously.

7. The combination according to claim 6, wherein each administration comprises a single dose or a continuous perfusion.

8. The combination according to claim 1, wherein said platinum coordination complex is carboplatin.

9. The combination according to claim 8, for the treatnent of metastatic breast cancer.

* * * * *